United States Patent [19]

Mameniskis et al.

[11] 4,287,132

[45] Sep. 1, 1981

[54] PREPARATION OF POLYISOCYANATES FROM POLYCARBAMATES

[75] Inventors: Walter A. Mameniskis, Drexel Hill; Frank W. Melpolder, Wallingford, both of Pa.

[73] Assignee: Atlantic Richfield Company, Los Angeles, Calif.

[21] Appl. No.: 191,543

[22] Filed: Sep. 29, 1980

[51] Int. Cl.³ .................. C07C 118/00; C07C 125/07
[52] U.S. Cl. .................................. 260/453 P; 560/25
[58] Field of Search ...................... 260/453 P; 560/25

[56] References Cited

U.S. PATENT DOCUMENTS

| | | | |
|---|---|---|---|
| 2,946,768 | 7/1960 | Klauke et al. | 560/25 |
| 3,919,279 | 11/1975 | Rosenthal et al. | 260/453 P |
| 3,962,302 | 6/1976 | Rosenthal et al. | 260/453 P |
| 4,014,914 | 3/1977 | Pistor | 260/453 PH |
| 4,146,727 | 3/1979 | Shawl et al. | 560/25 |

FOREIGN PATENT DOCUMENTS 2425658 12/1974 Fed. Rep. of Germany .

*Primary Examiner*—Dolph H. Torrence
*Attorney, Agent, or Firm*—Delbert E. McCaslin

[57] ABSTRACT

In the process of producing a diisocyanate comprising
(a) condensing and rearranging alkyl phenylcarbamate and formaldehyde under acidic conditions to form dialkyl methylene bis(phenylcarbamate) and
(b) thermally decomposing the dialkyl methylene bis(phenylcarbamate) to diphenylmethane diisocyanate, the improvement comprises prior to step (b) treating the reaction product of (a) by first distilling the reaction product of (a) under reduced pressure at a temperature below 120° C. until all solvent is removed and 65–85% of the unreacted alkyl phenylcarbamate present is removed, discontinuing the distillation, adding a polar solvent to undistilled distillation residue and selectively crystallizing and separating dialkyl methylene bis(phenylcarbamate) from the distillation residue.

5 Claims, No Drawings

PREPARATION OF POLYISOCYANATES FROM POLYCARBAMATES

FIELD OF THE INVENTION

The present invention is an improvement in the process of producing polyisocyanates by pyrolyzing polyurethanes. A crude polyurethane reaction mixture is produced by acid catalyzed condensation-rearrangement of an alkyl N-aryl carbamate and formaldehyde and purified by removal by distillation of solvent and unreacted alkyl N-aryl carbamate and isolating pure polyurethane by selective solvent crystallization.

BACKGROUND OF THE INVENTION

Polymeric aromatic carbamic acid esters (polyurethanes) such as diphenylmethane dicarbamates and the related higher homologs, polymethylene polyphenyl carbamates, have become increasingly important products particularly, for use in the preparation of the commercially valuable diphenylmethane diisocyanates and mixtures of diisocyanates and the polyisocyanates by the decomposition of such polymeric aromatic carbamic acid esters in a suitable solvent as shown in Rosenthal et al, U.S. Pat. Nos. 3,962,302 and 3,919,279.

Diphenylmethane diisocyanates and polyisocyanates, available commercially, have been largely produced by the phosgenation of mixtures of diamines and polyamines obtained by the condensation of aniline and formaldehyde with catalytic quantities of a mineral acid as disclosed in Pistor et al, U.S. Pat. No. 4,014,914. German Pat. No. 2,425,658 describes a process wherein the polyisocyanate product of a phosgenation reaction was distilled under reduced pressure. An overhead temperature of 200°–30° C. at 2–2.5 mm. Hg. were the distillation conditions. The distillate mixtures contained 5 to 70% diphenylmethane diisocyanate (both 2,4' and 4,4' isomers). Cooling the distillate caused crystallization of both isomers of the product diphenylmethane diisocyanate.

A proposed prior art process for the preparation of polymeric aromatic carbamic acid esters (polyurethanes) is disclosed in Klauke et al U.S. Pat. No. 2,946,768 and involves the condensation of aryl carbamic acid esters with carbonyl compounds in a dilute aqueous acid condensation medium. However, in such process the carbonyl compound such as formaldehyde tends to react at the nitrogen of the carbamate to produce, along with desired polyurethanes, varying amounts, i.e., generally between 15 percent and 50 percent by weight, of undesirable (alkoxycarbonyl)-phenylaminomethylphenyl compounds which includes the various dimers, trimers, tetramers, etc. of such compounds (also referred to herein as "N-benzyl" compounds). Attempts to prepare mono or diisocyanates and polyisocyanates or to otherwise use the mixture containing the undesired N-benzyl compounds (which cannot be converted to an isocyanate by pyrolysis) and polyurethanes presents many problems since there is no known method for separating the polyurethanes from the N-benzyl impurities.

However, the undesired N-benzyl compounds may be catalytically rearranged to a desired polyurethane in accordance with the teachings of Shawl et al, U.S. Pat. No. 4,146,727. Accordingly, a product mixture from a condensation as disclosed in aforementioned U.S. Pat. No. 2,946,768 containing diurethanes and polyurethanes, N-benzyl compounds, unreacted alkyl phenyl carbamates and other by-products such as amines may be contacted at temperatures of from about 50° C. to 170° C. with a protonic acid medium having a strength at least equal to a 75 percent sulfuric acid such as concentrated sulfuric acid or an acid medium comprising a Lewis acid having a concentration of at least 0.5 percent by weight based on the total reaction mixture, while maintaining a minimum amount of water in the system, to catalytically convert or rearrange said N-benzyl compounds.

Even after rearrangement of the N-benzyl compounds the reaction mixture contains an undesirable amount of detrimental by-products, unreacted starting material and solvent. In order to obtain good yields of polyisocyanate with the maximum content of isocyanate moieties, it would be ideal to enrich or maximize the polyurethane content of the reaction mixture relative to the other components.

SUMMARY OF THE INVENTION

Alkyl phenylcarbamate and formaldehyde are subjected to acidic condensation and rearrangement to produce a crude reaction product of dialkyl ester of methylene bis(phenylcarbamic acid). According to the present invention high quality dialkyl ester of methylene bis(phenylcarbamic acid) is obtained by a two step process which involves first distilling the crude reaction product to remove solvent and unreacted alkyl phenyl carbamate starting material and then isolating the alkyl ester of methylene bis(phenylcarbamic acid) by selective solvent crystallization from the distilland.

It is an object of this invention therefore to obtain a purified dialkyl ester of methylene bis(phenylcarbamic acid).

It is another object of the present invention to permit obtaining a superior diphenylmethane diisocyanate by pyrolysis when the pyrolysis feed is a solution of the dialkyl ester of methylene bis(phenylcarbamic acid) enriched according to this invention.

These and other objects and advantages of this invention will become apparent from the description of the invention which follows and from the claims.

DESCRIPTION OF THE INVENTION

The dialkyl ester of methylene bis(phenylcarbamic acid) is produced from alkyl phenylcarbamate and formaldehyde as follows:

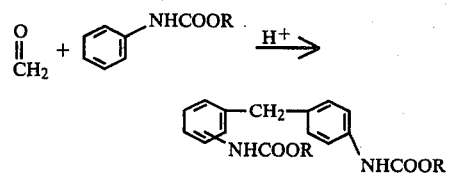

wherein R is alkyl having 1 to 3 carbon atoms.

When ethyl phenyl carbamate and formaldehyde are subjected to acidic condensation and rearrangement according to methods known in the art from aforementioned U.S. Pat. Nos. 2,946,768 and 4,146,727 a product mixture having the following average composition by weight percent is obtained after waste water removal:

| | |
|---|---|
| ethyl phenylcarbamate | 35% |
| 4,4'-diethyl methylene bis(phenylcarbamate) | 11% |
| 2,4'-diethyl methylene | |

| | |
|---|---|
| bis(phenylcarbamate) | 2.4% |
| Heavies | 1.5% |
| Solvent (i.e., nitrobenzene) | 50% |

A product mixture of the above composition may be used directly as a feedstock to a pyrolysis step wherein the carbamate moieties are thermally decomposed to isocyanate moieties. However, it is more desirable to have a feed which is much richer in 4,4'-diethyl methylene bis(phenylcarbamate). Such an enriched feed may be obtained by the process according to this invention.

A product mixture having the above average composition is subjected to vacuum distillation whereby all the solvent (i.e., nitrobenzene) is removed along with 65–85% of the ethyl phenylcarbamate present. The temperature of the still-pot should not exceed 120° C. in order to prevent thermal decomposition of the carbamate moieties to isocyanate moieties, aniline and other undesirable products. After removal of solvent and 65–85% of ethyl phenylcarbamate present, distillation is discontinued and the distillation pot bottoms (distilland) subjected to selective solvent crystallization to recover 4,4'-diethyl methylene bis(phenylcarbamate).

To effect the crystallization, the distillation pot bottoms rich in 4,4'-diethyl methylene bis(phenylcarbamate) are dissolved in a polar solvent with the bottoms to solvent weight ratio being 0.5 to 1.0. The preferred solvent is ethanol. Other suitable solvents include methanol, n-propanol, isopropanol, nitromethane, nitroethane, acetonitrile and propionitrile. Of course, the dialkyl methylene bis(phenylcarbamate) must be in solution in order to be crystallized from the solvent and hence, it must be soluble in the solvent chosen. Solvents such as nitrobenzene and diphenyl ether also produce high quality crystals of 4,4'-diethyl methylene bis(phenylcarbamate) but with lower yields. Temperatures employed for the crystallization step range from an upper limit defined by the boiling point of the solvent chosen down to a lower limit of about 10° C. Using ethanol as a solvent the crystallization temperature ranges from 78° to 10° C. and preferably from 75° to 25° C. Preferably the solvent is added to the distillation pot bottoms at the upper end of the crystallization temperature range and the mixture cooled to the lower end of the temperature range whereupon formed crystals of 4,4'-diethyl methylene bis(phenylcarbamate) are removed from the solution.

The following Examples are provided to illustrate the invention in accordance with the principles of this invention but are not to be construed as limiting the invention in any way except as indicated by the appended claims.

EXAMPLE 1

A mixture having the following composition was charged into a distillation vessel.

| | Weight % |
|---|---|
| 4,4'-diethyl methylene bis(phenylcarbamate) | 10.1 |
| 2,4-diethyl methylene bis(phenylcarbamate) | 2.2 |
| ethyl phenylcarbamate | 31.9 |
| Heavies | <0.3 |
| nitrobenzene | 54.6 |

The mixture was distilled under reduced pressure until all nitrobenzene was removed and 65% of the ethyl phenylcarbamate was removed whereupon distillation was discontinued. The distillation temperature was about 111° C. and the final distillation pressure was about 2 mm Hg. The mixture remaining in the distillation vessel had the following composition by weight percentage.

| | |
|---|---|
| 4,4'-diethyl methylene bis(phenylcarbamate) | 42.6 |
| 2,4'-diethyl methylene bis(phenylcarbamate) | 8.9 |
| ethyl phenylcarbamate | 42.0 |
| Heavies | 5.9 |

The mixture was allowed to cool to about 70° C. whereupon ethanol was added to the vessel with stirring. The mixture continued to cool and stirring was continued until the mixture reached about 24° C. The mixture was then filtered and solid crystals containing 98.1% by weight 4,4'-diethyl methylene bis(phenylcarbamate), 2.3% ethyl phenylcarbamate and 0.48% heavies were recovered. The yield of 4,4'-diethyl methylene bis(phenylcarbamate) was about 40%.

Recrystallization of the filter cake from ethanol led to 4,4'-diethyl methylene bis(phenylcarbamate) of about 100% purity with a yield of about 83.1%.

EXAMPLE 2

The procedure of Example 1 was repeated using an initial feed mixture of the following composition.

| | Weight % |
|---|---|
| 4,4'-diethyl methylene bis(phenylcarbamate) | 10.4 |
| 2,4'-diethyl methylene bis(phenylcarbamate) | 2.1 |
| ethyl phenylcarbamate | 32.0 |
| Heavies | 1.4 |
| nitrobenzene | 54.0 |

The mixture was distilled until all nitrobenzene and 85% of the ethyl phenylcarbamate present had been removed whereupon distillation was stopped. The resulting mixture in the distillation vessel had the following composition by weight percentage.

| | |
|---|---|
| 4,4'-diethyl methylene bis(phenylcarbamate) | 53.4 |
| 2,4'-diethyl methylene bis(phenylcarbamate) | 10.8 |
| ethyl phenylcarbamate | 24.2 |
| Heavies | 6.3 |

After adding ethanol, cooling and filtering as in Example 1 a crystalline product was obtained containing 92.1% by weight 4,4'-diethyl methylene bis(phenylcarbamate), 1.0% 2,4'-diethyl methylene bis(phenylcarbamate), 3.4% ethyl phenylcarbamate and 1.6% heavies. The yield of 4,4'-diethyl methylene bis(phenylcarbamate) was about 50%.

Recrystallization of the crystalline product led to 4,4'-diethyl methylene bis(phenylcarbamate) of about 100% purity with a yield of about 86.6%.

What is claimed is:
1. In the process of producing a diisocyanate comprising

(a) condensing and rearranging formaldehyde and alkyl phenylcarbamate with the alkyl having 1 to 3 carbon atoms under acidic conditions to form alkyl methylene bis(phenylcarbamate) with the alkyl having 1 to 3 carbon atoms and (b) thermally decomposing the dialkyl methylene bis(phenylcarbamate) to diphenylmethane diisocyanate, the improvement comprises prior to step (b) treating the reaction product of (a) by first distilling the reaction product of (a) under reduced pressure at a temperature below 120° C. until all solvent is removed and 65 to 85% of the unreacted alkyl phenylcarbamate present is removed, discontinuing the distillation, adding a polar solvent to undistilled distillation residue and selectively crystallizing and separating dialkyl methylene bis(phenylcarbamate) from the distillation residue.

2. The process according to claim 1 wherein the polar solvent is ethanol.

3. The process according to claim 1 wherein the amount of polar solvent added to the distillation residue is in a ratio of 0.5 to 1.0 parts solvent per part of residue by weight.

4. The process according to claim 1 wherein the selective crystallization is conducted at 78° to 10° C.

5. The process according to claim 1 wherein the dialkyl methylene bis(phenylcarbamate) is diethyl methylene bis(phenylcarbamate).

* * * * *